(12) United States Patent
Culha

(10) Patent No.: US 8,435,753 B2
(45) Date of Patent: May 7, 2013

(54) TISSUE DIFFERENTIATION METHOD BASED ON SURFACE ENHANCED RAMAN SCATTERING

(75) Inventor: Mustafa Culha, Islanbul (TR)

(73) Assignee: Yeditepe Universitesi, Istanbul (TR)

( * ) Notice: Subject to any disclaimer, the term of this patent is extended or adjusted under 35 U.S.C. 154(b) by 163 days.

(21) Appl. No.: 12/936,197

(22) PCT Filed: Apr. 1, 2009

(86) PCT No.: PCT/IB2009/051367
§ 371 (c)(1),
(2), (4) Date: Dec. 27, 2010

(87) PCT Pub. No.: WO2009/122363
PCT Pub. Date: Oct. 8, 2009

(65) Prior Publication Data
US 2011/0124014 A1   May 26, 2011

(30) Foreign Application Priority Data
Apr. 1, 2008 (TR) ............................... a 2008 02195

(51) Int. Cl.
*G01N 33/574* (2006.01)
(52) U.S. Cl.
USPC ........................................ 435/7.23; 435/7.21
(58) Field of Classification Search .................. None
See application file for complete search history.

(56) References Cited

U.S. PATENT DOCUMENTS

| | | |
|---|---|---|
| 5,864,397 A | 1/1999 | Vo-Dinh et al. |
| 2005/0147979 A1 | 7/2005 | Koo et al. |

OTHER PUBLICATIONS

Kah J.C.Y. et al., Early diagnosis of oral cancer based on the surface plasmon resonance of gold nanoparticles, International Journal of Nanomedicine, 2007, vol. 2, No. 4, pp. 785-798.*
Culha M. et al., Surface-enhanced Raman scattering for cancer diagnostics: detection of the BcL2 gene, Expert Review of Molecular Diagnostics, Sep. 2003, vol. 3, No. 5, pp. 669-675.*
Haynes C.L. et al., Plasmon-Sampled Surface-Enhanced Raman Excitation Spectroscopy, J. Phys. Chem. B, 2003, vol. 107, pp. 7426-7433.*
International Search Report, mailing date Oct. 7, 2009, for corresponding International Application No. PCT/IB2009/051367.
Written Opinion of the International Searching Authority, mailing date Jan. 10, 2010, for corresponding International Application PCT/IB09/051367.

* cited by examiner

*Primary Examiner* — Jon P Weber
*Assistant Examiner* — Satyendra Singh
(74) *Attorney, Agent, or Firm* — Intellectual Property Law Group LLP

(57) ABSTRACT

This invention is related to sample preparation by a tissue differentiation method based on surface-enhanced Raman scattering (SERS) which enables fast and accurate pathological identification for tissue differentiation by means of surface-enhanced Raman scattering. The preparation of the sample includes homogenising a tissue sample by adding liquid nitrogen (104), crushing the frozen tissue and bringing it to a liquefied form (105).

1 Claim, 2 Drawing Sheets

TISSUE DIFFERENTIATION METHOD BASED ON SURFACE ENHANCED RAMAN SCATTERING

CROSS-REFERENCE TO RELATED APPLICATIONS

Figure 1:
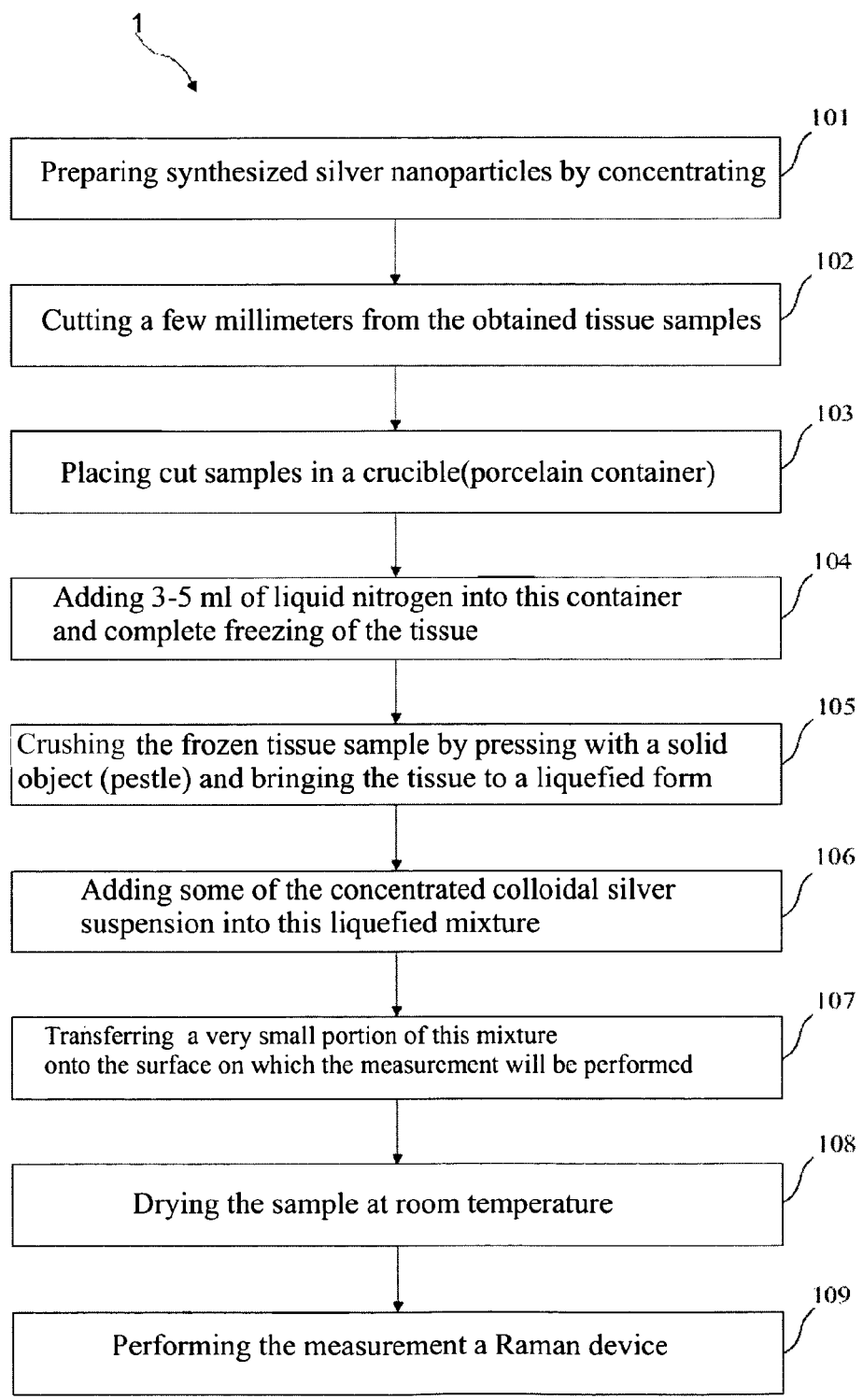

This application is a U.S. National Phase application, under 35 U.S.C. §371, of International Application no. PCT/IB2009/051367, with an international filing date of Apr. 1, 2009 and claims benefit of Turkish Application no. 2008/02195 filed on Apr. 1, 2008, and which are hereby incorporated by reference for all purposes.

FIELD OF THE INVENTION

This invention is related to a sample preparation method to be used for surface-enhanced Raman scattering (SERS) technique in order to ensure fast and accurate pathological identification of the changes in tissues occurring due to the formation of a variety of diseases.

BACKGROUND ART

SERS, which is a vibrational spectroscopic technique, is a type of Raman scattering which is performed near to surfaces comprising nano-scaled structures formed of metals such as gold, silver, or copper, or surfaces of nanoparticles prepared from the said metals, and which provides detailed information about the chemical structure of the molecule under investigation. The enhancement effect is the result of the charge transfer between the molecule under investigation and the nanostructured metal surface, and mostly the surface plasmon formation resulting from the overlapping of the frequency of the laser directed onto the analyzed sample and the oscillation frequencies of the electrons which enable conductivity of metal nanoparticles. Therefore, it is necessary to create surfaces where surface plasmons can be utilized effectively for improved enhancement.

The pathological identification of human tissue samples especially in cancerous tissues is difficult. This difficulty becomes more pronounced with certain tumor types. The conventional pathological tumor identification is performed by eye examination or certain spectroscopic techniques. The pathologist examines the sample by eye and after staining with several staining methods and other techniques, tries to identify whether the tissue sample is tumorous or healthy or the degree of the tumor. The pathological identification of tissue samples with spectroscopic techniques can be faster and more reliable. The conventional pathological tissue differentiation methods are methods which require detailed investigation on the sample, and through which, it is sometimes difficult to obtain an accurate result despite the said detailed investigation. Therefore, in the recent years, using the spectroscopic techniques for differentiation that is based on the composition of the molecular structures composing the tissue has increased in importance. One of the most important spectroscopic techniques applied in the present day is vibrational spectroscopy. There is a number of studies and methods related to these techniques based on IR, NIR and Raman. All these approaches have their own specific difficulties and disadvantages. While water in the sample can be a problem in IR based techniques, Raman requires increased spectral collection times since scattering is very weak, and the data obtained by using both IR and Raman techniques should definitely be evaluated statistically.

The U.S. Pat. No. 5,261,410 known in the art discloses a method that can differentiate if a tissue sample is malignant, benign or a normal tissue. This invention claims that when the sample is irradiated with NIR light, different tissue samples generate distinguishable Raman spectra.

The U.S. Pat. No. 5,261,410 and international patent No. WO2008001978 known in the art describe the use of silica nanoparticles prepared with silver nanoparticles in a surface-enhanced Raman scattering based method. The method in the invention is claimed that it can be used in detection of specific diseases such as leukemia and breast cancer.

SUMMARY OF THE INVENTION

The objective of this invention is to prepare tissue samples to be used in SERS technique for fast pathological identification of tissues taken from patients for diagnosis purposes and to identify whether the tissue is diseased/tumorous or healthy based on the changes on the spectra obtained from these samples by means of SERS technique.

Another objective of this invention is to develop a tissue differentiation method based on SERS technique which will guide in deciding until what point should the tumor be cut and removed.

DETAILED DESCRIPTION OF THE INVENTION

The sample preparation method realized to fulfill the objectives of the present invention and the changes in the surface-enhanced Raman scattering spectrum is illustrated in the accompanying figures, in which, FIG. 1 is a flow chart demonstrating the sample preparation method for surface-enhanced Raman scattering.

Figure 2:
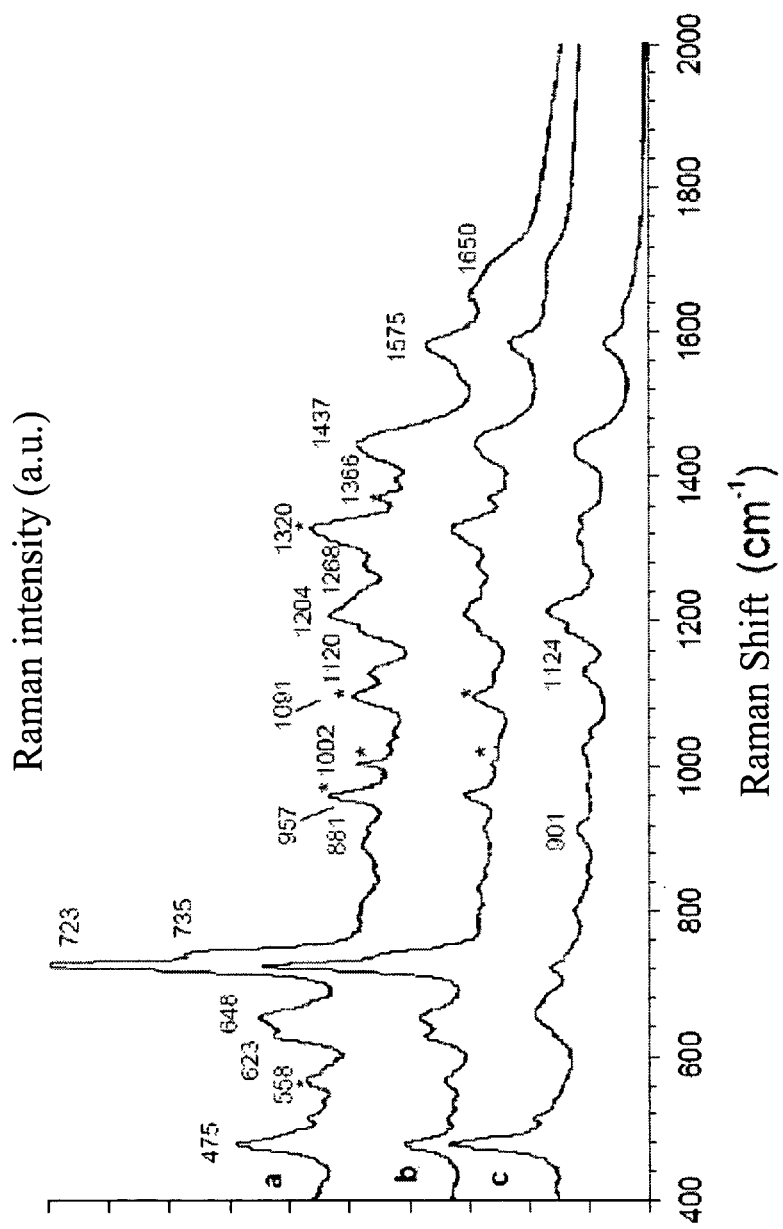

FIG. 2 shows the surface-enhanced Raman scattering spectra obtained from samples prepared with b) brain tumor, b) peripheral tissue surrounding the tumor, and c) healthy tissue using the inventive method.

The pieces/parts on the figures are numbered and the information corresponding the numbers is presented below.

1. A tissue differentiation method based on surface-enhanced Raman scattering
   a. Tumor
   b. Peripheral tissue surrounding the tumor
   c. Healthy tissue The inventive method of sample preparation for tissue differentiation based on surface-enhanced Raman scattering comprises the following steps, Preparing synthesized silver nanoparticles by concentrating (101), Cutting a few millimeters from the obtained tissue samples (102), Placing cut samples in a crucible (porcelain container) (103), Adding 3-5 ml of liquid nitrogen into this container and complete freezing of the tissue (104), Crushing the frozen tissue sample by pressing with a solid object (pestle) and bringing the tissue to a liquefied form (105), Adding some of the concentrated colloidal silver suspension into this liquefied mixture (106), Transferring a very small portion of this mixture onto the surface on which the measurement will be performed (107), Drying the sample at room temperature (for about 10 min.) (108) and Performing the measurement with a Raman device (109).

With the inventive method (1), whether the tissues are healthy or tumorous can be determined easily and with a high accuracy. In the said method, the tissue that will be identified is placed in a container. A certain amount of liquid nitrogen is added into this container and the tissue is completely frozen. The frozen tissue is crushed with a solid object for liquefying. With this crushing and liquefying process, the tissue sample is ensured to be homogeneous. The silver and/or gold colloidal nanoparticles are added into the crushed liquefied tissue. The tissue sample is dried at room temperature within about 10 min and after it is dried, the tissue identification is completed by means of the Raman device.

FIG. 2 shows the SERS spectra of a brain tumor, peripheral tissue surrounding the tumor, and healthy tissue obtained from the samples prepared with the inventive method. As seen on the figure, the spectral differences can be easily distinguished even with eye. On the figure, "a", "b", and "c" represent the tumor, the peripheral tissue surrounding the tumor, and the healthy tissue, respectively. With this method, the doctor can obtain information regarding tissue differentiation in a short time.

The invention claimed is:

1. A tissue differentiation method based on surface enhanced Raman scattering, which enables rapid tissue identification and enables determining, during surgery, an area where a cancerous tissue is located; the method comprising the steps of:
   preparing synthesized silver and/or gold nanoparticles, in which silver and/or gold colloidal solutions are used, by concentrating (101),
   cutting a few millimeters from a plurality of obtained tissue samples (102),
   placing the plurality of cut tissue samples in a porcelain container (103),
   adding 3-5 ml of liquid nitrogen or argon into the container and completely freezing the cut tissue samples (104), hereinafter referred to as "frozen tissue sample",
   crushing the frozen tissue sample by pressing with a solid object and bringing the frozen tissue sample to a liquefied mixture (105),
   adding a part of the silver/and or gold nanoparticles directly into the liquefied tissue mixture (106), hereinafter referred to as "mixture sample",
   transferring a small portion of the mixture sample onto a surface on which measurement will be performed (107),
   drying the mixture sample at room temperature (108)
   performing a measurement with a Raman device (109).

* * * * *